(12) United States Patent
Kirk et al.

(10) Patent No.: US 10,413,683 B2
(45) Date of Patent: Sep. 17, 2019

(54) DEVICE AND METHOD FOR DISCHARGING A REACTIVE LIQUID

(71) Applicant: Nordson Corporation, Westlake, OH (US)

(72) Inventors: Thomas A. Kirk, Hastings, MN (US); Bradley D. Robb, Maple Plain, MN (US); Todd W. Sharratt, Stillwater, MN (US)

(73) Assignee: Nordson Corporation, Westlake, OH (US)

( * ) Notice: Subject to any disclaimer, the term of this patent is extended or adjusted under 35 U.S.C. 154(b) by 590 days.

(21) Appl. No.: 14/920,781

(22) Filed: Oct. 22, 2015

(65) Prior Publication Data

US 2016/0038693 A1 Feb. 11, 2016

Related U.S. Application Data

(62) Division of application No. 13/798,201, filed on Mar. 13, 2013, now Pat. No. 9,174,001.

(Continued)

(51) Int. Cl.
*A61M 11/06* (2006.01)
*B05B 7/06* (2006.01)
(Continued)

(52) U.S. Cl.
CPC .......... *A61M 11/06* (2013.01); *A61M 5/2448* (2013.01); *A61M 13/00* (2013.01);
(Continued)

(58) Field of Classification Search
CPC .... A61M 11/06; A61M 5/2448; A61M 13/00; A61M 11/00; A61M 11/007; B05B 7/061; B05B 7/2472
See application file for complete search history.

(56) References Cited

U.S. PATENT DOCUMENTS 3,739,983 A 6/1973 Jousson
6,706,023 B1 3/2004 Huttner et al.
(Continued)

FOREIGN PATENT DOCUMENTS

EP 0692273 A1 1/1996
EP 1955660 A2 8/2008
(Continued)

OTHER PUBLICATIONS

European Patent Office, European Search Report in EP Application No. 13180074, dated Nov. 6, 2013.
European Application No. 13180074.0: Office Action dated Oct. 7, 2016, 7 pages.

*Primary Examiner* — Edelmira Bosques
(74) *Attorney, Agent, or Firm* — Baker & Hostetler LLP

(57) ABSTRACT

A device and method for dispensing a liquid with a gas includes an instrument having a cannula and a low-pressure tip. The low-pressure tip includes a tip housing that at least partially defines a high pressure chamber. A distal wall of the tip housing includes an aperture in fluid communication with the high pressure chamber. The low-pressure tip also includes a tube and a gas flow channel. The tube fluidly communicates liquid at a relatively low pressure from the cannula through the first aperture. The gas flow channel fluidly communicates gas from the cannula at a relatively high pressure and to the high pressure chamber for discharge from the aperture. The tube and aperture are adapted to dispense the liquid and the gas in order to create a low pressure zone distal of the tube to dispense droplets of the liquid.

8 Claims, 3 Drawing Sheets

Related U.S. Application Data

(60) Provisional application No. 61/681,760, filed on Aug. 10, 2012.

(51) Int. Cl.
*A61M 11/00* (2006.01)
*B05B 7/00* (2006.01)
*A61M 5/24* (2006.01)
*A61M 13/00* (2006.01)
*B05B 7/24* (2006.01)
*B05B 11/02* (2006.01)

(52) U.S. Cl.
CPC ............ *B05B 7/061* (2013.01); *B05B 7/2472* (2013.01); *A61M 11/007* (2014.02); *A61M 2202/0225* (2013.01); *B05B 7/0081* (2013.01); *B05B 7/2464* (2013.01); *B05B 7/2497* (2013.01); *B05B 11/02* (2013.01)

(56) References Cited

U.S. PATENT DOCUMENTS

| | | |
|---|---|---|
| 7,611,494 B2 | 11/2009 | Campbell et al. |
| 2002/0165483 A1 | 11/2002 | Miller et al. |
| 2008/0272209 A1 | 11/2008 | Yokoyama et al. |
| 2008/0294099 A1 | 11/2008 | Yatabe et al. |
| 2009/0199848 A1 | 8/2009 | Sharratt |
| 2012/0000993 A1* | 1/2012 | Brunk ............ A61B 17/00491 239/306 |
| 2012/0305669 A1* | 12/2012 | Meron ............ A61B 17/00491 239/428 |

FOREIGN PATENT DOCUMENTS

| | | |
|---|---|---|
| EP | 2000215 A2 | 12/2008 |
| WO | 2008144871 A2 | 12/2008 |
| WO | 2009001393 A1 | 12/2008 |

\* cited by examiner

DEVICE AND METHOD FOR DISCHARGING A REACTIVE LIQUID

CROSS-REFERENCE TO RELATED APPLICATION

This application is a divisional of application Ser. No. 13/798,201, filed Mar. 13, 2013, which is a non-provisional of Application Ser. No. 61/681,760 filed Aug. 10, 2012, the disclosures of which are hereby incorporated by reference herein.

TECHNICAL FIELD

The present invention relates generally to a low-pressure tip and method for dispensing a liquid with a gas from a cannula, and more particularly, to a low-pressure tip configured to dispense reactive liquids and gas for use in a surgical procedure.

BACKGROUND

Generally, it is well-known to dispense liquids in the form of "sprayed" droplets for use in surgical procedures. More specifically, a plurality of reactive liquids may be sprayed under the influence of pressurized gas to disperse and dispense the droplets on the human body or within the human body to beneficially affect the outcome of the surgical procedure. For instance, two highly reactive fluids may be sprayed onto an anatomical site for reducing the flow of blood by hemostatic clotting or creating tissue barriers to prevent anatomical tissues from adhering together during and/or after the surgical procedure. Ideally, these reactive liquids are isolated prior to being discharged from the instrument. As such, the reactive liquids mix and react once discharged from the instrument for application at the anatomical site. Thus, the beneficial characteristics of the reacting fluids are preserved until needed for use.

Traditionally, prior to discharging the reactive fluids, the reactive fluids are mixed with high pressure gas within a high pressure chamber of the tip so that the reactive fluids form the sprayed droplets. Many fluids, such as these reactive fluids, prematurely activate or react under the influence of the high pressure. In the event of a premature reaction between the reactive fluids, the beneficial characteristics are greatly, if not completely, reduced upon application to the anatomical site. Thus, the benefits of the surgical procedure are not fully realized in the event of the premature reaction between liquids.

There is a need for an apparatus and method for use in dispensing a liquid with a gas from a cannula, such as during a surgical procedure, that addresses present challenges and characteristics such as those discussed above.

SUMMARY

An exemplary embodiment of a device for dispensing a liquid with a gas for use in a surgical procedure includes an instrument having a cannula and a low-pressure tip. The low-pressure tip has a tip housing that includes a distal wall and at least partially defines a high pressure chamber within the tip housing. The distal wall has a first aperture in fluid communication with the high pressure chamber. In one aspect, the proximal portion of the tip housing is adapted for attachment to the cannula. More particularly, the proximal portion of the tip housing is attached to the cannula of the instrument.

The low-pressure tip also includes a first tube and a first gas flow channel. The first tube is adapted to fluidly communicate the liquid at a relatively low pressure from the cannula to distally beyond the high pressure chamber through the first aperture. In addition, the first gas flow channel is adapted to fluidly communicate the gas from the cannula at a relatively high pressure to the high pressure chamber for discharging the gas from the first aperture. Accordingly, the first tube and the first aperture are adapted to dispense the liquid and the gas for creating a low pressure zone distal of the first tube in order to dispense droplets of the liquid.

In another aspect, the low-pressure tip also includes a tip adapter, and at least a portion of the tip housing defines a cavity. The tip adapter includes the first gas flow channel and the first tube extending therethrough. The tip adapter is positioned at least partially within the cavity such that the distal wall and the tip adapter further define the high pressure chamber. As such, the first tube extends through the tip adapter and is configured to insert into the cannula for communicating liquid therethrough.

In use, a method for dispensing a first liquid with a gas from a low-pressure tip includes fluidly communicating the gas through the first gas flow channel into the high pressure chamber. The method also includes discharging the first liquid from a distal end of the first tube and discharging the gas from the high pressure chamber through the first aperture. In addition, the method includes passing the gas over the distal end of the first tube and creating a low pressure zone distal of the first tube. The method further includes spraying the first liquid with the gas and forming droplets from the first liquid.

Furthermore, in one aspect of use, the method includes fluidly communicating the gas through the second gas flow channel into the high pressure chamber. The method also includes discharging the second liquid from a distal end of the second tube and discharging the gas from the high pressure chamber through the second aperture. In addition, the method includes passing the gas over the distal end of the second tube and creating a low pressure zone distal of the second tube. The method further includes spraying a second liquid with the gas and forming droplets from the second liquid.

In another aspect, the method of forming droplets also includes mixing the first and second liquids to create droplets having both first and second liquids.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

DETAILED DESCRIPTION

Figure 1:
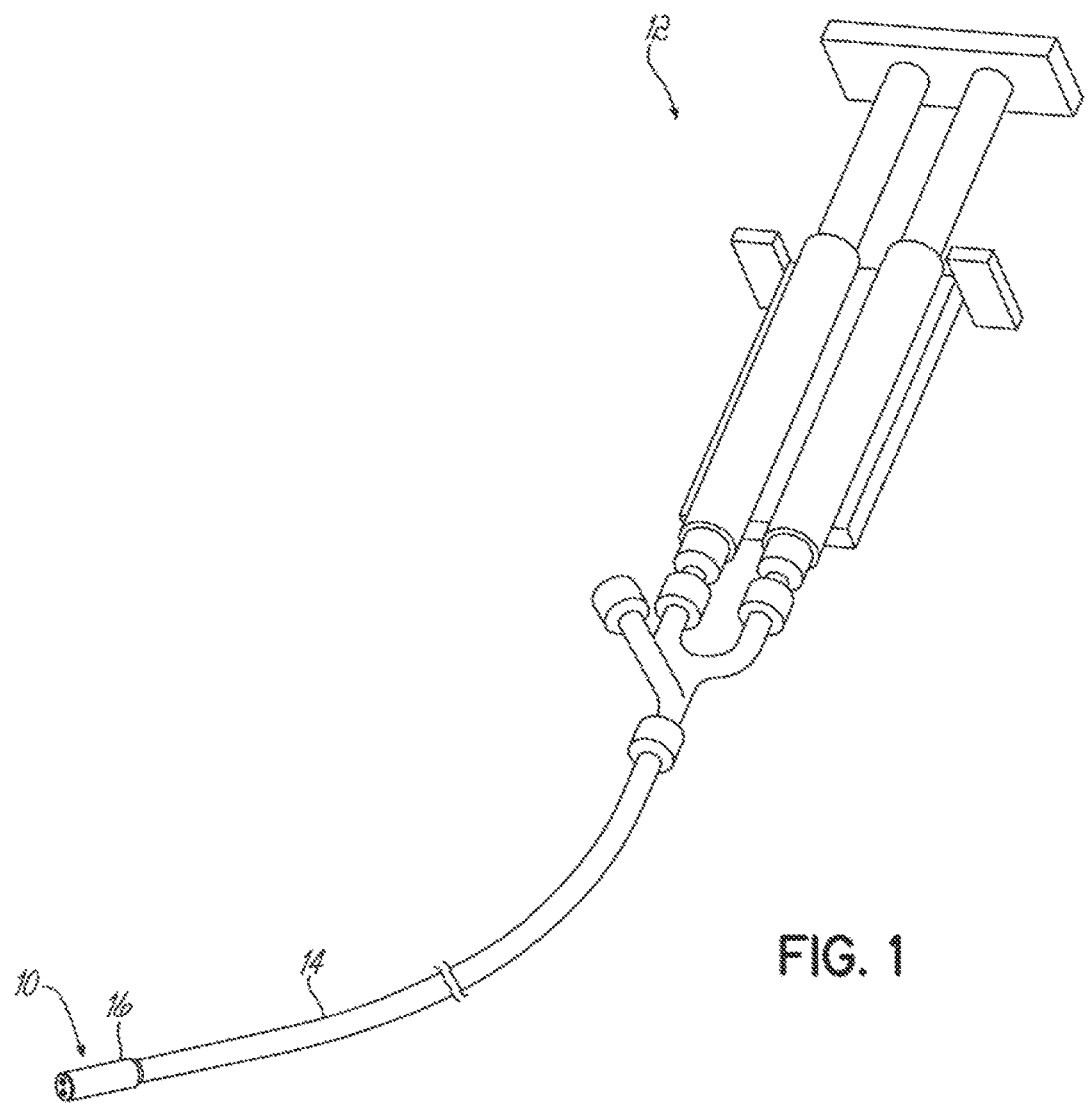
FIG. 1 is a perspective drawing of one embodiment of an instrument having a low-pressure tip.
Figure 1A:
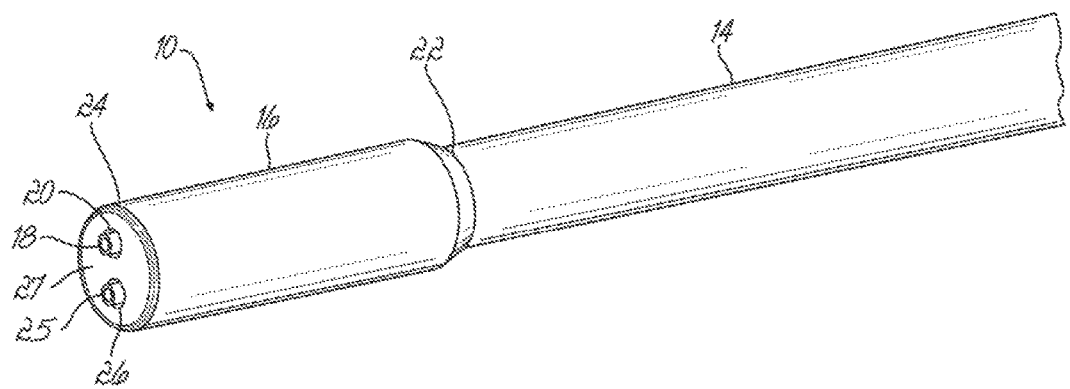
FIG. 1A is a perspective drawing of the low-pressure tip of FIG. 1 attached to a cannula of the instrument.

With reference to FIGS. 1-1A, an exemplary embodiment of the low-pressure tip 10 for dispensing a reactive liquid with a gas, particularly with respect to instruments used in surgical procedures, is attached to an instrument 12 having a cannula 14. While the low-pressure tip 10 may be used with any appropriate gas assisted liquid dispensing instrument or device, examples of such devices include applicators sold under the FibriJet® name by Nordson Micromedics, of St. Paul, Mn. The cannula 14 may be rigid, flexible, or flexible and steerable. The applicator 12 may be manual, such as those that utilize one or more manually actuated syringes, or may be powered in any desirable manner. In any case, the cannula 14 is adapted to be in fluid communication with the low-pressure tip 10 for delivering a pressurized fluid to the low-pressure tip 10. Generally, the applicator 12 may be any medical instrument used for dispensing reactive liquids with a gas, such that the reactive liquids dispense as droplets for application on a desirable surface. More particularly, the cannula 14 of the applicator 12 is adapted to deliver a plurality of reactive liquids and a gas to the low-pressure tip 10 for dispensing droplets from the low-pressure tip 10 onto an anatomical site during medical procedures. Such medical procedures for use with the low-pressure tip 10 may include topical applications, open surgical applications, and minimally invasive applications such as laparoscopy.

The exemplary embodiment of the low-pressure tip 10 is generally cylindrically shaped and includes a tip housing 16, a hypodermic tube 18, and a gas aperture 20. The tube 18 and the aperture 20 are each in fluid communication with the applicator 12. Generally, the low-pressure tip 10 is adapted to be connected to the cannula 14 at a proximal end portion 22 of the tip 10. In addition, the tube 18 and the aperture 20 are in fluid communication with the cannula 14 and are adapted to dispense the liquid from the tube 18 and the gas from the aperture 20 at a distal end portion 24 of the tip 10. More particularly, the exemplary embodiment of the invention includes a pair of tubes 18, 25 for dispensing first and second reactive fluids, such as first and second reactive liquids, and a pair of apertures 20, 26 for dispensing a single, generally inert gas around the first and second reactive liquids, such as $CO_2$ or air. It will be appreciated, however, that any number of tubes and apertures may be respectively used with any number of reactive liquids and gases, and the invention is not intended to be limited to the exemplary embodiment.

With respect to the tip housing 16, the proximal end portion 22 is adapted to be connected to the cannula 14. The proximal end portion 22 is also tapered to reduce the lip between the tip housing 16 and the cannula 14 for improving performance of the low-pressure tip 10 during use. For instance, tapering the proximal end portion 22 reduces the likelihood that the low-pressure tip 10 will catch on an external communicating device, such as a trocar, while being removed. The cannula 14 is inserted into the low-pressure tip 10 in order to place the applicator 12 in fluid communication with the pair of tubes 18 and apertures 20. Each of the first and second liquids and the gas are isolated from each other within the low-pressure tip 10. Accordingly, the distal end portion 24 of the tip housing 16 includes a wall 27 through which the apertures 20 extend, that separates the gas from the reactive liquids. However, as the gas is fluidly communicated distal of the wall 27 and the liquid is fluidly communicated distal of the tube 20, the fluids mix to form liquid droplets.

Figure 2:
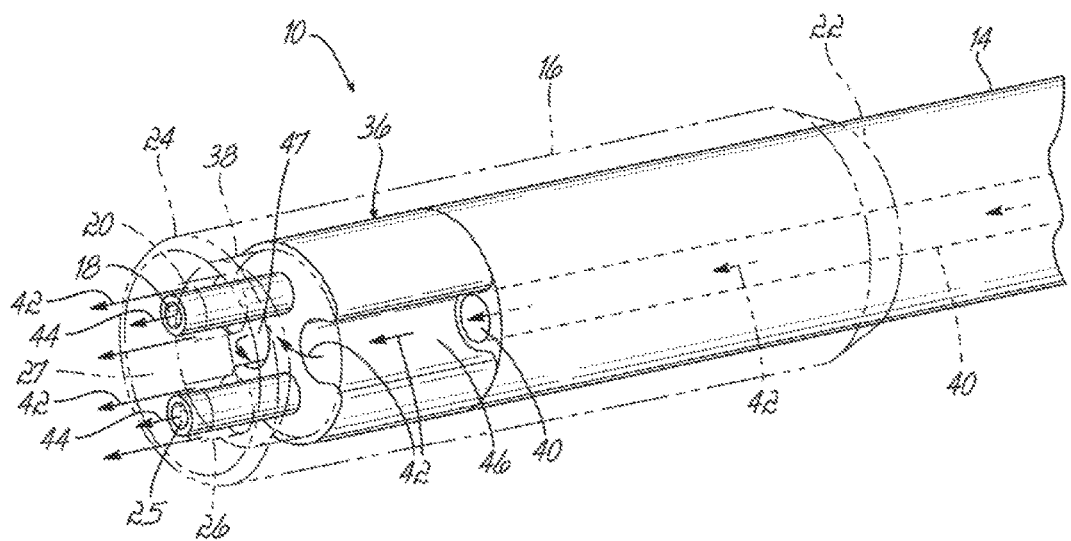
FIG. 2 is a perspective drawing of the low-pressure tip of FIG. 1 having the tip housing shown by hidden lines.
Figure 3:
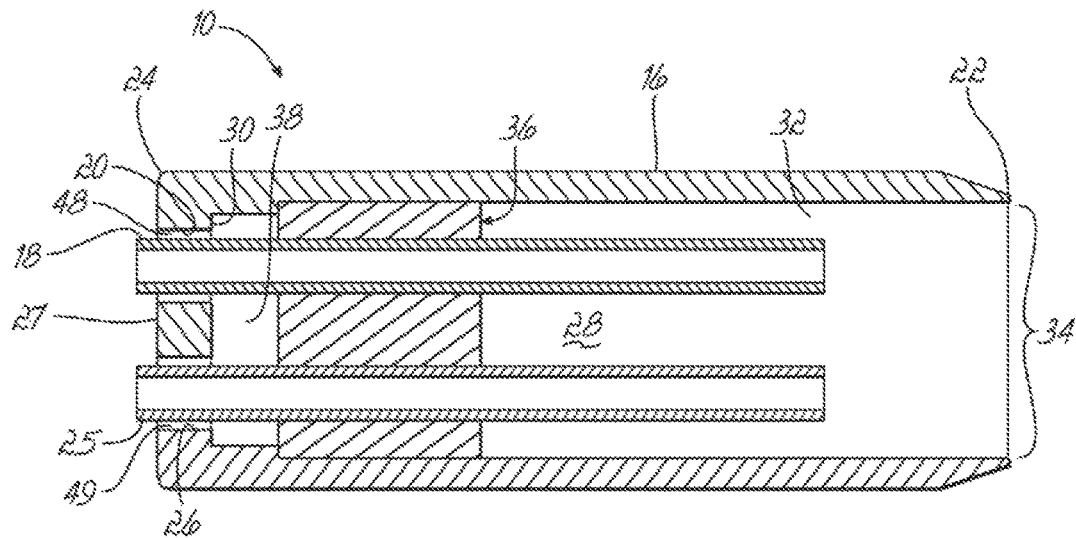
FIG. 3 is a cross-sectional side view of the low-pressure tip of FIG. 1.

As shown in FIGS. 2-3, the tip housing 16 defines an interior cavity 28 therein. According to the exemplary embodiment, the interior cavity 28 has a distal cavity portion 30 and a proximal cavity portion 32. The proximal cavity portion 32 has an opening 34 at the proximal end portion 22 and is sized and adapted such that the cannula 14 is sealably inserted therein. Moreover, a tip adapter 36 is inserted into at least a portion of the interior cavity 28 between the distal cavity portion 30 and the cannula 14. Accordingly, the tip adapter 36, the wall 27, and the distal cavity portion 30 define a high pressure chamber 38 in fluid communication with both the apertures 20 and a pair of gas lumens 40, 41 (see FIGS. 2 and 4) within the cannula 14 adapted to deliver the pressurized gas (as indicated by arrows 42).

The tip adapter 36 receives the tubes 18, 25 as each extends through the tip adapter 36 and reaches proximal from the tip adapter 36 for insertion into the reactive fluid lumen (not shown) within the cannula 14. Thereby, the tubes 18, 25 are fluidly connected with the reactive liquids from the cannula 14. The tubes 18 also extend distally from the tip adapter 36 through the high pressure chamber 38 and through at least a portion of the apertures 20. As shown in the exemplary embodiment, each of the tubes 18, 25 terminates distal of the wall 27 for discharging reactive liquid (as indicated by arrows 44).

Moreover, the tip adapter 36 includes a gas flow channel 46 in fluid communication with the gas lumen 40 and the high pressure chamber 38 for transporting high pressure gas from the gas lumen 40 to the pressurized chamber 38. According to the exemplary embodiment, the tip adapter 16 includes a pair of gas flow channels 46, 47; however, it will be appreciated that any number of gas flow channels 46, 47 may be so used. While the gas flow channels 46, 47 are isolated from each other, their fluid communication into the high pressure chamber 38 is commonly shared such that the high pressure gas from each of the gas flow channels 46, 47 enters the high pressure chamber 38 for discharge through the apertures 20, 26. For example, the pressure of the gas 42 within the high pressure chamber 38 is approximately 5 psi. However, the input pressure at the proximal end will typically be higher to account for pressure drop between the proximal and distal ends of the applicator 12 and/or low-pressure tip 10. Such pressure of the pressurized gas 42 has been shown to work well for applications in which the reactive liquids 44 comprise blood and thrombin for causing hemostatic clotting at an anatomical site.

The high pressure, pressurized gas 42 discharges through a pair of circumferential flow gaps 48, 49 defined by the circumferential space between each of the tubes 18, 25 and the respective apertures 20, 26. As such, the high pressure gas discharges from the pair of circumferential flow gaps 48, 49 surrounding the tubes 18, 25 distal of the wall 27.

Figure 4:
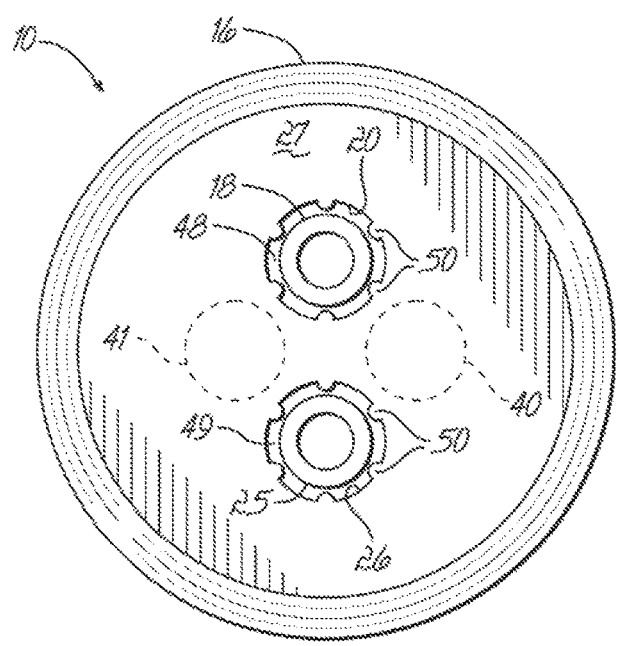
FIG. 4 is a front view of the low-pressure tip of FIG. 1.

FIG. 4 shows the generally central and vertically symmetrical placement of the apertures 20, 26 and the tubes 18, 25 extending therethrough from the wall 27 to the cannula 14. The wall 27 is shown as being generally flat. However, the wall 27 may also be modified in a variety of configurations for producing any one of a variety of spray patterns or configurations. Moreover, the gas lumens 40 are shown relatively central and horizontally symmetrical through the cannula 14. In addition, the wall 27 may include a plurality of nodes 50 extending at least partially into the pair of flow gaps 48, 49. The plurality of nodes 50 are generally symmetrically positioned surrounding the pair of tubes 18, 25 and configured to maintain the flow gaps 48, 49 surrounding the tubes 18, 25. Accordingly, the plurality of nodes 50 prevents each of the tubes 18, 25 from traveling either vertically or horizontally within the respective apertures 20, 26 in order to maintain the circumferential placement of each flow gap 48, 49. Thereby, the pressurized gas discharges generally circumferentially and uniformly around the tubes 18, 25. It will be appreciated, however, that vertical and horizontal directions are intended to be relative to the exemplary embodiment in FIG. 4, and that such directions are not intended to limit the invention. Generally, the cannula 14 includes the pair of gas lumens 40, 41 and a pair of reactive liquid lumens (not shown) in fluid communication with the tubes 18, 25 as described herein. However, a fifth lumen (not shown) may be provided for the steerable/flexible cannula for holding a steerable guide wire so that a doctor, or similar practitioner, may more accurately and easily direct the low-pressure tip 10 to a desired target.

In order to use the low-pressure tip 10 with the applicator 12, the low-pressure tip 10 is inserted onto the cannula 14 of the applicator 12 so that the tubes 18, 25 align with the reactive liquid lumens (not shown) and the gas flow channels 46, 47 align with the gas lumens 40, 41. The tubes 18, 25 are in fluid communication with the reactive liquid lumens and dispense the reactive fluids, at relatively low pressure, distal of the tubes 18, 25. The gas flow channels 46, 47 are in fluid communication with the gas lumens 40, 41 such that the gas, at relatively high pressure, travels through the gas flow channels 46, 47 and enters the high pressure chamber 38.

The high pressure chamber 38 forces the gas circumferentially through the flow gaps 48, 49 surrounding the tubes 18, 25 at a relatively high pressure. Generally, the velocity of the gas is greater than the velocity of the reactive liquids; however, the gas discharges through the apertures 20, 26 having laminar flow. As the laminar flow of the gas passes distally over the tubes 18, 25, a low pressure zone is created at each of the discharging reactive liquids. The low pressure zone further accelerates each of the reactive liquids causing the reactive liquids to discharge or "spray" from the low-pressure tip with the gas. This spray of the reactive liquids creates droplets of the reactive liquids for application during medical procedures, such as surgery. Thereby, the reactive liquids are not mixed or formed into droplets while at the relatively high pressure in order to prevent the reactive liquids from prematurely reacting at the high pressure for proper application.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A method for dispensing first and second liquids with a gas from a low-pressure tip having a tip housing with first and second apertures, a high pressure chamber, first and second gas flow channels that are isolated from each other, and first and second tubes respectively extending through the first and second apertures, the method comprising:
   fluidly communicating the gas independently through the first and second gas flow channels and discharging the gas from the first and second gas flow channels into the high pressure chamber;
   discharging the first liquid from a distal end of the first tube and the second liquid from a distal end of the second tube;
   discharging the gas from the high pressure chamber through the first and second apertures;
   passing the gas over the distal ends of the first and second tubes;
   creating a low pressure zone distal of the first and second tubes;
   spraying the first and second liquids with the gas; and
   forming droplets from the first and second liquids.

2. The method of claim 1, wherein spraying the first and second liquids further comprises discharging the gas with a greater velocity than the first and second liquids to create the low pressure zone that accelerates the first and second liquids.

3. The method of claim 1, wherein:
   the first liquid is a first reactive liquid and the second liquid is a second reactive liquid, and
   forming droplets further comprises reacting the first and second reactive liquids to create droplets having both the first and second reactive liquids therein.

4. The method of claim 3, wherein the first reactive liquid is blood and the second reactive liquid is thrombin, the method further comprising spraying the blood and thrombin onto an anatomical site.

5. A method for dispensing first and second liquids with a gas from a low-pressure tip having a tip housing with first and second apertures, a high pressure chamber, first and second gas flow channels that are isolated from each other, and first and second tubes respectively extending through the first and second apertures, wherein the high pressure chamber is interposed between the first and second apertures and outlets of the first and second gas flow channels, the method comprising:
   fluidly communicating the gas independently through the first and second gas flow channels into the high pressure chamber;
   discharging the first liquid from a distal end of the first tube and the second liquid from a distal end of the second tube;
   discharging the gas from the high pressure chamber through the first and second apertures;
   passing the gas over the distal ends of the first and second tubes;
   creating a low pressure zone distal of the first and second tubes;
   spraying the first and second liquids with the gas; and
   forming droplets from the first and second liquids.

6. The method of claim 5, wherein spraying the first and second liquids further comprises discharging the gas with a greater velocity than the first and second liquids to create the low pressure zone that accelerates the first and second liquids.

7. The method of claim 5, wherein:
   the first liquid is a first reactive liquid and the second liquid is a second reactive liquid, and
   forming droplets further comprises reacting the first and second reactive liquids to create droplets having both the first and second reactive liquids therein.

8. The method of claim 7, wherein the first reactive liquid is blood and the second reactive liquid is thrombin, the method further comprising spraying the blood and thrombin onto an anatomical site.

* * * * *